United States Patent [19]
May et al.

[11] Patent Number: 5,972,910
[45] Date of Patent: Oct. 26, 1999

[54] DELIVERY SYSTEM FOR ANTIMETHANOGENIC AGENTS

[75] Inventors: Christopher May, Heidelberg Heights; Alan Lindsay Payne, Beaumarls; Philip Laurence Stewart, Eltham; John Alexander Edgar, Carlten, all of Australia

[73] Assignee: Commonwealth Scientific and Industrial Research Organisation, Campbell, Australia

[21] Appl. No.: 08/836,465

[22] PCT Filed: Nov. 3, 1995

[86] PCT No.: PCT/AU95/00733

§ 371 Date: Jul. 23, 1997

§ 102(e) Date: Jul. 23, 1997

[87] PCT Pub. No.: WO96/14062

PCT Pub. Date: May 17, 1996

[30] Foreign Application Priority Data

Nov. 4, 1994 [AU] Australia ................ PM9225

[51] Int. Cl.⁶ .................................. A61K 31/715
[52] U.S. Cl. .................................. 514/58
[58] Field of Search .................................. 514/58

[56] References Cited

FOREIGN PATENT DOCUMENTS

74531/91  9/1991  Australia.
79845/94  4/1995  Australia.

OTHER PUBLICATIONS

Canadian Journal of Animal Science, vol. 51, No. 3 (1971), Wood A.S. and Johnson, E.D., "Action of Antimethanogenic Agents on Diurnal Patterns of Fermentation Activity, Long Chain Fatty Acids, and Protozoa Count in Cattle", pp. 783–792.

Australian Journal of Agricultural Research, vol. 29, No. 6, (1978), Lanigan, G.W., et al, "Antimethanogenic Drugs and *Heliotropium europacum* Poisoning in Penned Sheep", pp. 1281–1292.

*Primary Examiner*—Kevin E. Weddington
*Attorney, Agent, or Firm*—McDermott, Will & Emery

[57] ABSTRACT

A delivery system is provided to reduce methane production in animals or to improve the weight gain of an animal. Embodiments include a delivery system comprising a volatile and/or water soluble antimethanogenic agent with cyclodextrin or a cyclodextrin-like compound.

5 Claims, 4 Drawing Sheets

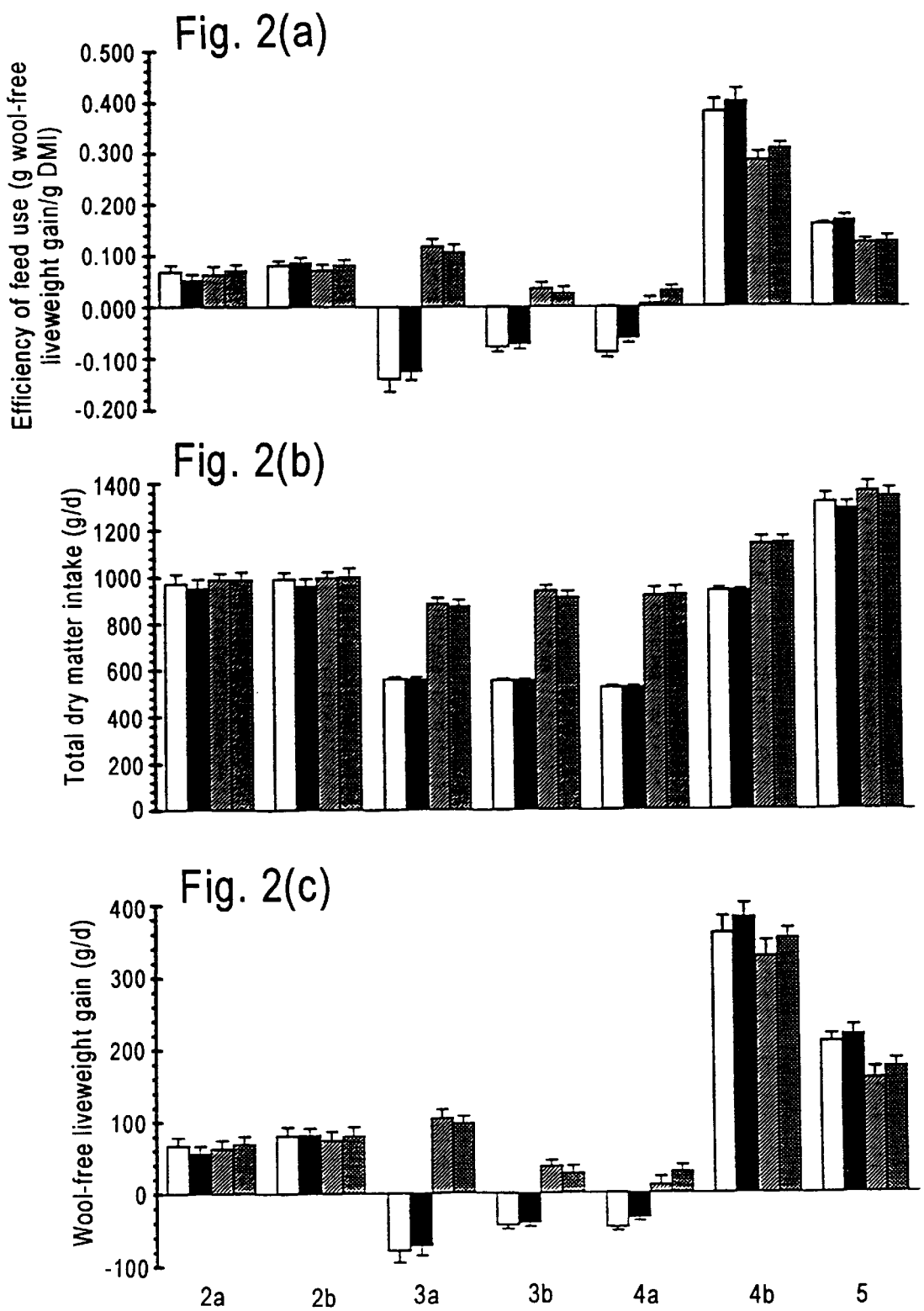

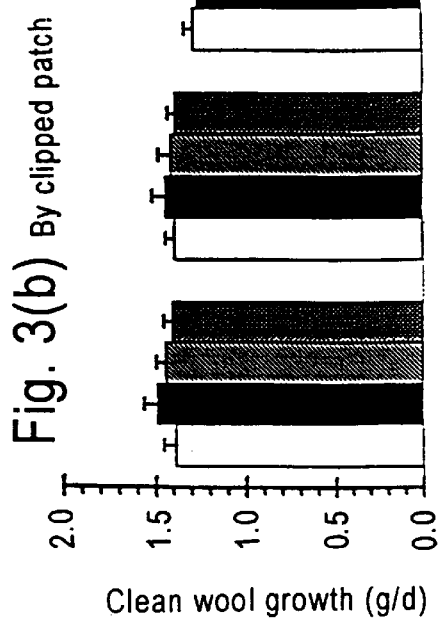
Fig. 3(b) By clipped patch
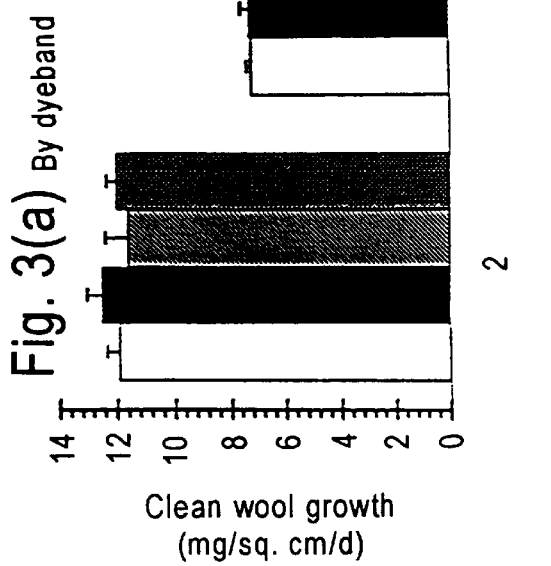
Fig. 3(a) By dyeband

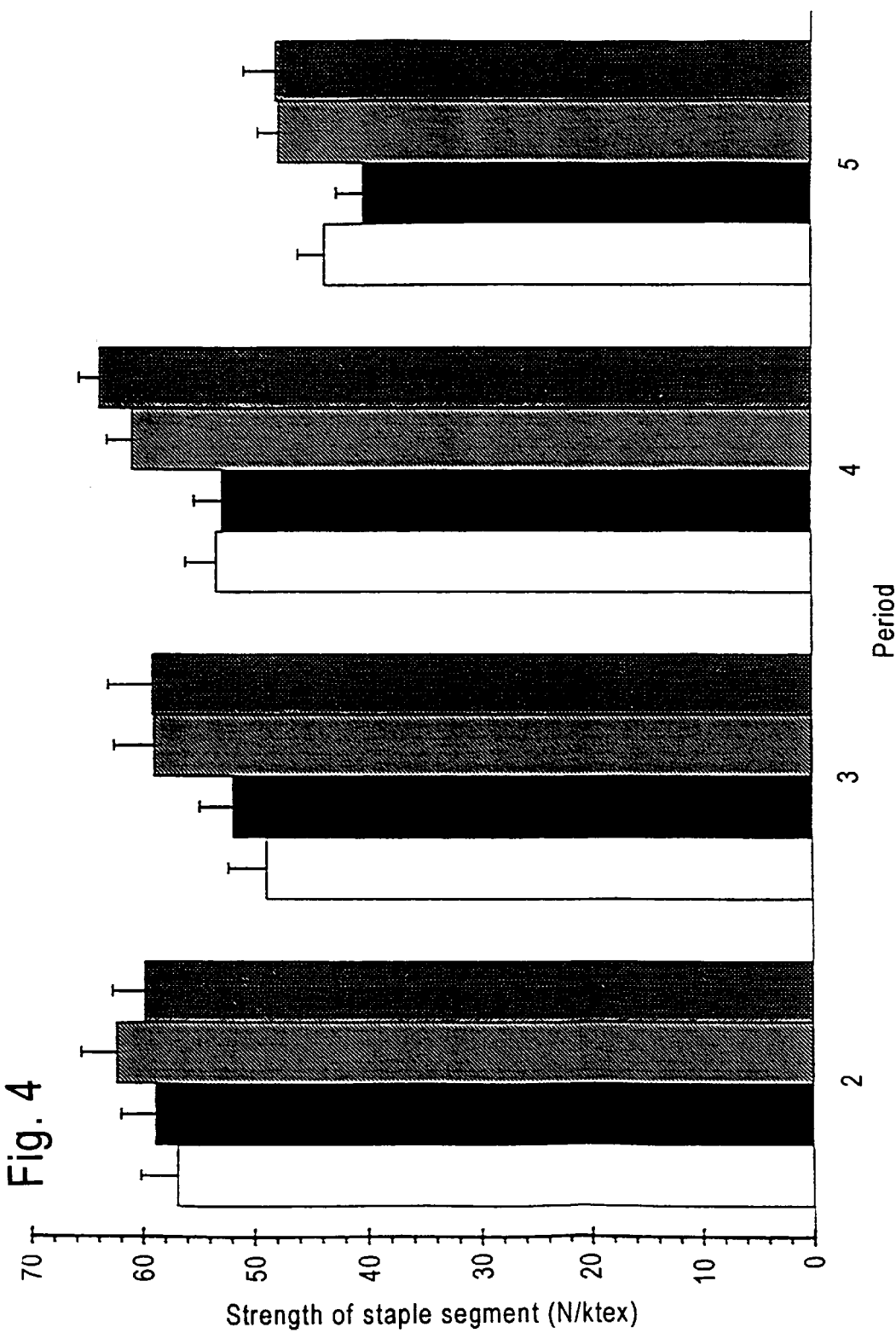

DELIVERY SYSTEM FOR ANTIMETHANOGENIC AGENTS

The present invention relates to a delivery system for delivering a volatile and/or water soluble antimethanogenic agent to an animal, a composition comprising the agent and methods of treatment of an animal.

BACKGROUND OF INVENTION

Microorganisms capable of generating methane are commonly found in the gut flora of animals including ruminants. The microorganisms which produce methane in ruminants result in the loss of energy available to the animal and are also believed to contribute significantly to greenhouse gases.

Specifically, it has been known for many years that suppression of methane production in ruminants can theoretically lead to increased production and much work has been undertaken to reduce methane biosynthesis and achieve production gains in domestic animals. This has been most successfully achieved by modifications to the diet of animals. Diet manipulation is only possible in a limited number of animal production systems and is generally only able to reduce and not completely suppress methane production. A number of approaches to methane suppression in animals are being explored, not only to increase animal production but also to reduce the level of methane in the environment because of its contribution to the "greenhouse" effect.

Bromochloromethane (BMC) and some other related substances are known to show antimethanogenic activity when administered into the rumen of cattle and sheep but they have physical properties which makes impractical their use as antimethanogens in livestock production systems, BCM for example is a volatile liquid, boiling point 69 C., which readily evaporates. Bromoethane sulphonate, another antimethanogen, is difficult to administer because it is water soluble.

While the antimethanogenic properties of BCM and other antimethanogens have been known for more than 25 years no one has identified a practical means of using them to suppress methane production in livestock and obtain production increases.

Thus there has been a long felt need in the animal production field to find a practical means of inhibiting methanogenesis in animals, in particular ruminants.

It may also be desirable to reduce methane production in other animals. Inhibition of methane production would reduce the environmental impact of animals. In the case of domestic animals that inhabit households, it may be desirable to reduce methane production to achieve more pleasant conditions.

Cyclodextrins are cyclic oligosaccharides which have been used in the pharmaceutical and food industries in the preparation of various formulations incorporating active ingredients.

SUMMARY OF THE INVENTION

It is an object of the present invention to overcome at least some of the difficulties of the prior art in delivering antimethanogenic agents to animals.

In work leading up to the present invention the inventors recognised the possibility that BMC and related antimethanogenic substances might form inclusion complexes with one or more cyclodextrins although these inclusion complexes had not been produced previously. It was also possible, but by no means certain, that these inclusion complexes might have properties which would enable them to be used as practical antimethanogens for suppressing methane production in animals.

The inventors have now demonstrated that inclusion complexes are formed with a number of antimethanogenic substances and show that these complexes have antimethanogenic properties and physical properties which made them suitable for administration of livestock by several available delivery processes. The BCM-α-cyclodextrin inclusion complex is shown for example to have properties particularly suitable for administration to livestock either as a feed additive or in a controlled release device, to suppress methane production and to give production benefits in cattle and sheep.

In its broadest form the present invention provides a delivery system for delivering a volatile and/or water soluble antimethanogenic agent to an animal, said system comprising a volatile and/or water soluble antimethanogenic agent with a cyclodextrin or cyclodextrin-like compound such that sustained release of said agent is provided.

DETAILED DESCRIPTION OF PREFERRED EMBODIMENTS

It has been surprisingly found by the present inventors that cyclodextrin complexed with a volatile and/or water soluble antimethanogenic agent delays release of the agent to provide prolonged or sustained release of the agent.

The term "volatile" used herein refers to the tendency of the agent to evaporate and generally refers to fluid substances.

The volatile and/or water soluble anti-methanogenic agent may be any antimethanogenic agent which is volatile and/or water soluble. The term refers to any compound not normally in a solid state which is capable of inhibiting methanogenesis in animals with the proviso that the compound is physiologically acceptable to animals. Such agents include bromochloromethane and analogues thereof such as bromochloroethane or bromochloropropane and other compounds such as halothane, 2-bromoethane sulphonate and 2-bromo-2-chloroethane sulphonate.

The cyclodextrin may be selected from α-cyclodextrin, β-cyclodextrin or γ-cyclodextrin or derivatives thereof which may be naturally and/or synthetically produced. The cyclodextrin-like compound may be any compound capable of slowing or controlling the release of said agent and includes mannose based ring compounds.

The term "such that sustained release of the agent is provided" means that the antimethanogenic agent and cyclodextrin or cyclodextrin-like compound are capable of dissociation whereupon the agent is released at a reduced rate compared to the agent administered on its own.

Accordingly in one aspect the invention provides an antimethanogenic composition for use in animals comprising a volatile and/or water soluble antimethanogenic agent together with a cyclodextrin or a cyclodextrin-like compound such that sustained release of the agent is provided.

The term "animals" used above refers to any animal in which it is desirable to deliver an antimethanogenic compound. Preferably the animals are mammals. The mammals will generally be domestic animals such as ruminants (cattle, sheep, goats, deer, elk, alpacas, llamas), and other animals including horses, pigs, dogs, cats, humans.

The antimethanogenic agent is at least partly enclosed in, confined by, or encapsulated by the cyclodextrin or cyclodextrin-like compound. Once the composition is administered the agent dissociates from the cyclodextrin or cyclodextrin-like compound. Preferably the cyclodextrin forms an inclusion complex with the agent.

Preferably the composition is a pharmaceutical or veterinary composition in order to comply with the various regulatory standards for such compositions in different countries.

The dose of the antimethanogenic agent is in the range from about 1 to 150 mg per kg. More preferably the dose range is from 1 to 120 mg per kg, still more preferably 1 to 50 mg, even more preferably from 1 to 20 mg, even more preferably from 1 to 10 mg per kg of body weight.

Preferably the composition is in a particulate form. More preferably the particles are 50–100 mesh BSM.

Alternatively preferably the composition may be in the form of a capsule such as a gelatin capsule or the capsules described in Australian Patents 520409, 558009 and 555998.

In another aspect the invention provides an animal feed comprising the composition of the invention described above together with a nutrient source. The animal feed may be for a vegetarian animal such as cows, sheep, etc. or for carnivores or omnivores such as pigs and dogs.

In one particularly preferred aspect the composition of the present invention is incorporated into lucerne pasture, hay, cereals, legumes, by-products from food industries and/or polenta in the case of domestic animals such as cattle. In the case of dogs and cats the composition may be incorporated into dried pet or moist pet food. The animal feed or pet food may comprise other active ingredients in addition to the composition of the present invention. Such active ingredients include hormones, particularly growth hormones such as hormonal growth promotant, antibacterial compounds such as ionophores including Rumensin and the like.

In another aspect the invention provides a method of producing an anti-methanogenic composition comprising a volatile and/or water soluble antimethanogenic agent together with a cyclodextrin or cyclodextrin-like compound, said method comprising mixing said anti-methanogenic agent with a cyclodextrin or cyclodextrin-like compound such that sustained release of the agent will be provided upon administration, and optionally bringing the composition into a suitable dosage form.

The antimethanogenic agent is at least partly enclosed in, confined by, or encapsulated by the cyclodextrin or cyclodextrin-like compound.

The composition of the present invention may be prepared by the technique described in Budai and Szejtli (1981).

The terms "antimethanogenic agent", "cyclodextrin" and "cyclodextrin-like compound" have the same meaning as given above.

Those skilled in the art will be familiar with the conditions necessary to produce the antimethanogenic composition.

In another aspect the present invention provides a method of administering an antimethanogen to an animal over an extended period comprising administering a composition comprising a volatile and/or water soluble antimethanogenic agent together with a cyclodextrin or cyclodextrin-like compound such that sustained release of the agent is provided, in a manner such that said composition is retained by said animal over said period.

The term "over an extended period" refers to a period of time which is longer than the time taken for the volatile and/or water soluble antimethanogenic agent to evaporate when it is not present in the composition.

The term "in a manner such that said composition is retained by said animal over said period" means that the composition is applied in a suitable manner to allow sustained release. In a ruminant for example administration may be provided in the form of a controlled release device or may be provided in the feed. In monogastric animals the composition will be administered in the feed or alone.

Where the animal in the method is a ruminant the method leads to increased weight gains. The method is also of benefit in both ruminants and non-ruminants in that it reduces greenhouse gas emissions. In addition the method is also beneficial in humans and household pets where the antimethanogenic effects lead to reduced flatulence.

In a particularly preferred embodiment the invention relates to a method of reducing methane production in an animal over an extended period comprising administering a methane reducing effective amount of an antimethanogenic composition said composition comprising volatile and/or water soluble antimethanogenic compound together with a cyclodextrin or cyclodextrin-like compound such that sustained release of said agent is provided.

The antimethanogenic compound is at least partly enclosed by, confined by or encapsulated by the cyclodextrin or cyclodextrin-like compound.

In a related aspect the present invention provides a method of prolonging methane reduction in an animal where an antimethanogenic compound is administered to said animal, said method comprising administering a volatile and/or water soluble antimethanogenic compound complexed with a cyclodextrin or cyclodextrin-like compound such that sustained release is provided to said animal.

In another related aspect the present invention provides a method of improving weight gain in a ruminant comprising administering to said ruminant an effective amount of the composition of the invention for a time and under conditions sufficient to allow weight gain to occur.

The inventors have found that treatment of ruminants which are being fed on heliotrope with the antimethanogenic composition of the present invention leads to increased rumen metabolism of heliotrine. Presumably this leads to reduced toxicity in the animals. Thus the present invention also extends to a method of increasing pyrrolizidine alkaloid metabolism in a ruminant feeding on material containing pyrrolizidine alkaloids comprising administering to said ruminant an effective amount of a volatile and/or water soluble antimethanogen which is complexed with a cyclodextrin or cyclodextrin-like compound in accordance with the invention.

Preferably the antimethanogenic agent is at least partly enclosed in, confined by, or encapsulated by the cyclodextrin or cyclodextrin-like compound.

The dose of the antimethanogen may be in the range from about 1 to 150 mg per kg of body weight although those skilled in the art will be able to establish an effective administration dose for the particular application.

The composition may be administered by means of an intra ruminal control release device, in the form of granulated powder, in animal feed, or any other appropriate means.

In their work on the present invention, the inventors have surprisingly found that administration of an antimethanogen to sheep results in decreased wool fibre diameter.

Accordingly in another aspect the present invention provides a method of reducing wool fibre diameter in a wool producing animal comprising administering an effective amount of an antimethanogenic agent for a time and under conditions sufficient to allow wool growth.

The term "reducing wool fibre diameter" means to reduce the diameter of the wool fibre compared to the diameter of the fibre produced in an animal when not treated by the method.

The term "wool" used above refers to any natural fibre grown by an animal and includes wool, hair and other fibres whether or not they are keratin based.

The term "wool producing animal" includes any animal which produces wool or hair which is desirable to harvest. This includes sheep, goats (Cashmere and Angora), rabbits, alpacas and llamas and the like. Preferably the animal is a ruminant. More preferably the animal is a sheep or a goat.

The term "for a time and under conditions sufficient to allow wool growth" means that the treatment must be carried out for a sufficient length of time, in the wool growing season (where applicable) and under adequate nutritional and other conditions to allow the animal to produce wool Preferably the treatment is carried out over an extended period of time so that the wool grown is of a reduced diameter along its length.

The antimethanogenic agent may be any antimethanogenic agent. Preferably the antimethanogenic agent is administered as part of the composition of the present invention, however the method is not so limited.

The dose of the antimethanogenic agent may be in the range from about 1 to 150 mg per kg, preferably 1 to 50 mg per kg, more preferably 1 to 20, still more preferably 1 to 10 mg per kg of animal.

BRIEF DESCRIPTION OF THE DRAWINGS

The invention will now be described with reference to the following non-limiting Figures and Examples. Specifically while the invention is exemplified with reference to ruminants the invention is understood to be clearly applicable to non-ruminant animals.

FIGS. 2(a)–2(c). Rates of (a) liveweight gain, (b) dry matter intake and (c) efficiency of feed use for liveweight gain in weaner sheep with restricted (R; plain) or ad libitum (U; hatched) intakes of a roughage diet in Periods 3 and 4a and fed a supplement without (−AM; □ ▨) or containing an antimethanogen (+AM; ■ ▨) during Period 3, 4 and 5. All sheep were fed a mixed roughage and concentrate diet during Periods 2, 4b and 5.

FIGS. 3(a) and (b), Rates of change in clean wool growth, measured u sing (a) dyebands or (b) by clipping mid-side patches, in weaner sheep with restricted (R; plain) or ad libitum (U; hatched) intakes of a roughage diet in Period 3 and part of Period 4 (4a) and fed a supplement without (−AM; □ ▨) or containing an antimethanogen (+AM; ■ ▨) during Period 3, 4 and 5. All sheep were fed a mixed roughage and concentrate diet ad libitum in Periods 2, 4b and 5.

FIG. 4. Strength of segments of the full staple in weaner sheep with restricted (R; plain) or ad libitum intake of a mixed roughage and concentrate diet in Period 5 and fed a supplement without (−AM; □ ▨) or containing an antimethanogen (+AM; ■ ▨) during all periods.

EXAMPLE 1

Production of Antimethanogenic Composition

Figure 1:
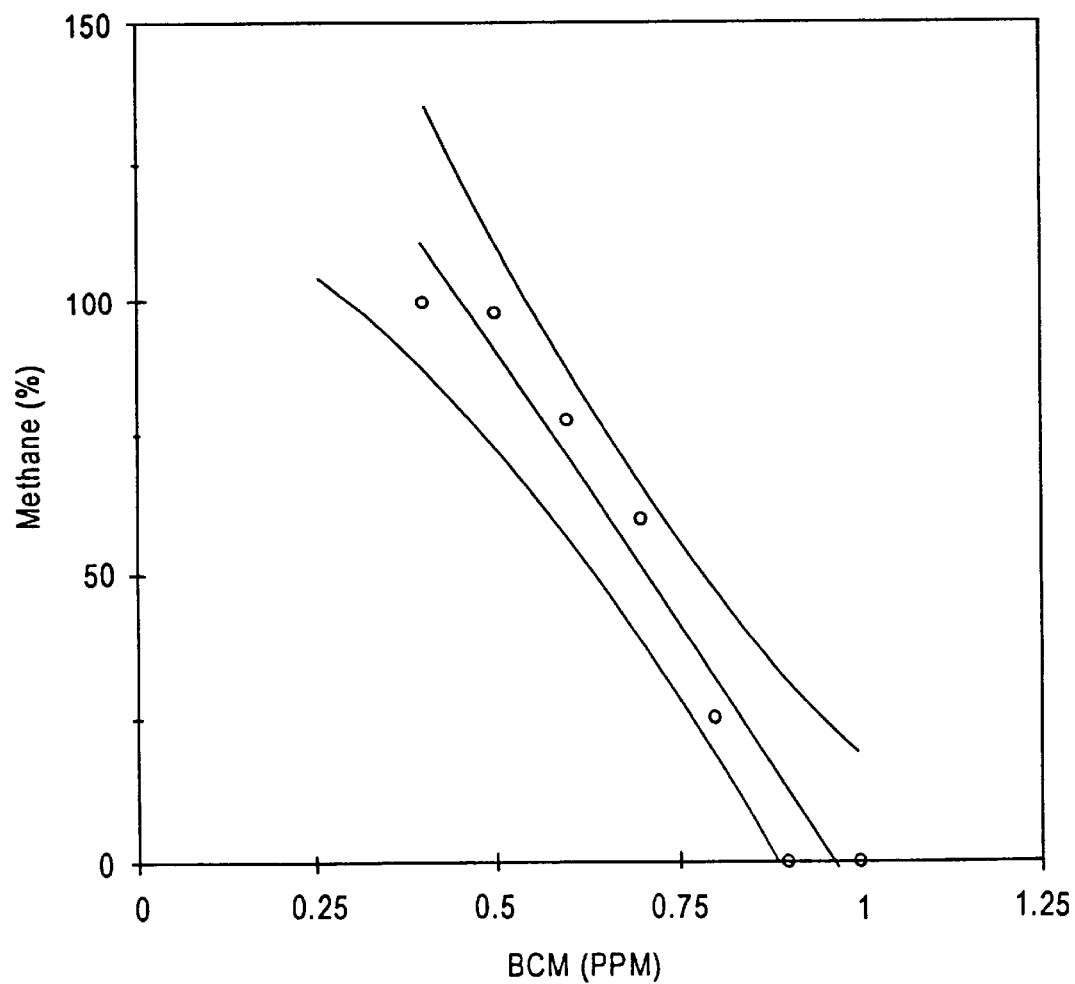
FIG. 1 is a graph showing the amount of methane as percentage of hydrogen and methane produced as a function of the amount of BCM (ppm) in a fixed volume of rumen fluid. The middle line represents the least squares best fit line. The upper and lower lines are the 95% confidence limits.

The manufacture of a molecular complex between an antimethanogen and cyclodextrin modifies the physical properties of the antimethanogen turning a liquid into a stable solid which substantially reduces the volatility of the antimethanogen and forms a stable complex. The complex acts as controlled release mechanism gradually releasing the guest as it slowly dissolves.

Materials and Methods:

Composition (complex): α-cyclodextrin (200 grams) was dissolved in water (1400 ml). The resulting solution was then vigorously stirred and bromochloromethane (BCM) (20 ml) was added. The resulting suspension was continuously mixed for 12 hours and then filtered and air dried at ambient temperature. The white solid (220 g) was then crushed and sieved to a particle size of 50 to 100 British Standard Mesh (BSM). The complex results in a composition containing 12% BCM and 88% cyclodextrin by weight.

A similar composition was made comprising the gas halothane which is also an antimethanogenic agent.

Another similar composition was produced using β-cyclodextrin with BCM.

Capsule formulation: the above composition was mixed with palmitic acid and SDS (both having comparable mesh size) in a tumble mixer for 12 hours and then pelleted in a pelleting machine to produce pellets of about 2 g each. Formulations were made with 0.5% and 0.1% SDS. Eight pellets were then placed in an intraruminal capsule in accordance with Australian Patent 558009 or 555998.

EXAMPLE 2

Study on Stability of the Complex

Materials and Methods:

The complex produced as described in Example 1 was used to determine the tolerance of the antimethanogen to environmental conditions which may be encountered in the field. The parameters tested were temperature (37, 45 and 60° C.) at a relative humidity of 55%, humidity (100% at 37° C.) and simulated sunlight (UVA and UBV irradiation) at 30° C. with a relative humidity of 55%.

The methane inhibiting activity of the antimethanogen in an in vitro fermentation system was used as an assay for the stability studies. The amount of antimethanogen needed to inhibit methane production in a measured amount of rumen fluid from an animal on a set diet, was demonstrated not to vary significantly over a period of a month, and therefore formed the basis for use of the rumen fluid in determining the amount of antimethanogen in a given sample. The protocol used was to place samples containing known amounts of the antimethanogen in chambers having the environments described above, one for each stability study. The samples were exposed to these environments for a period of up to 14 weeks with samples being withdrawn and used in the in vitro assay at regular intervals. In the rumen normally about 1% hydrogen and 99% methane is produced. Antimethanogenic activity refers to the amount of inhibition of methane production as measured by hydrogen production. A figure of 100% antimethanogenic activity means that 100% hydrogen and no methane is being produced. This means methanogenic activity is completely inhibited. A figure of 80% means that 80% hydrogen is being produced and 20% methane is produced. Table 1 gives the results of the studies at various temperatures with a relative humidity of 55% and the results from the test of stability at 30° C., relative humidity 55% under UV exposure.

TABLE 1

Stability of the complex at variOus temperatures with 55% relative humidity. The % expressed in the table is antimethanogenic activity (see above for definition).

| | Temperature | | | |
|---|---|---|---|---|
| Day | 37° C. | 45° C. | 60° C. | 30° C. +UV |
| 0 | 100% | 100% | 100% | 100% |
| 7 | — | 100% | 100% | 100% |
| 14 | 100% | 100% | 100% | 100% |
| 28 | 100% | 100% | 100% | 100% |
| 42 | 100% | 100% | 95% | — |
| 49 | — | — | — | 100% |
| 63 | — | — | 58% | — |
| 70 | 80% | 67% | — | 100% |
| 84 | 66% | — | — | — |
| 91 | — | 65% | 54% | — |
| 98 | — | — | — | 83% |

The stability studies at 37° C. with a relative humidity of 100% (not shown) demonstrated that antimethanogenic activity continued at 100% up to 14 days and then declined to 64% at 28 days, 10% at 70 days and 5% at 98 days.

Results:

From the stability studies indicate that the antimethanogen has the ability to tolerate elevated temperatures for quite substantial periods. The material completely retained its activity for 42 days at 37° and 45°, and completely retained its activity for 28 days at 60° C. Bromochloromethane has a boiling point of 68° C., the equivalent amount of this material placed in the above environments would evaporate in less than 12 hours. The complex material also appears to be stable when exposed to UV irradiation (simulated sunlight) completely retaining its activity for 49 days, although a loss of activity beyond this point may be in part due to the temperature in the irradiation chamber being at 30° C. At very high relative humidities it appears that the complex is not as stable.

EXAMPLE 3

Duration of Activity From a Single Dose

The incorporation of an antimethanogen into a complex enables its activity to be prolonged. This is due to the slow dissolution of the complex within the rumen of an animal and thus the gradual release of the active compound.

Materials & Methods:

An antimethanogenic complex in accordance with that made in Example 1 was used to dose a sheep and a steer. The doses were chosen to match prior art doses of BCM administered in the liquid form. Specifically Trei and Olson (1969) administered 53 mg of liquid BCM to a 40 kg sheep. This is equivalent to 440 mg of the complex of the present invention. The BCM administered by Trei & Olson (1969) resulted in antimethanogenic activity for 15 hours. Therefore we administered a single dose of 400 mg of the complex of the present invention to a 44 kg sheep.

Johnson et al (1972) administered a single dose of 5.5 g liquid BCM to a 450 kg steer. This resulted in complete inhibition of methane production for 6 hours. The dose used is equivalent to 46 g of the complex of the complex of the present invention. We administered a single dose of 5.4 g of the complex of the present invention.

Animals were given a single dose, a sample of rumen fluid was withdrawn and analysed as in Example 1.

Results:

In sheep the complex was shown to have substantial antimethanogenic activity 24 hours after administration (less than 20% normal methane production).

In cattle a single dose completely inhibited methane production in the treated animals for at least 24 hours.

EXAMPLE 4

Inhibition of Methane Production In Vitro

Materials & Methods: complex as produced in Example 1 was used in an in vitro assay similar to that described in Example 2.

Results:

BCM complex inhibits the production of methane in rumen fluid in vitro at a level of 5 ppm–7.5 pmm of complex and 0.6–0.9 ppm of BCM. This is shown in FIG. 1.

EXAMPLE 5

Long-term Inhibition of Methane Production in Cattle

Materials and Methods: as per Example 3 except cattle were studied for 15 weeks and the antimethanogen was only administered up to and including week 12.

Results

We demonstrate that the composition provides substantial methanogenic activity over an extended period. See Table 2.

TABLE 2

Average methane production as a percentage of Hydrogen + Methane in treated cattle.

| Week | Control | Antimethanogenic Composition |
|---|---|---|
| 0 | 85.8 | 83.5 |
| 1 | 91.5 | 0.5 |
| 2 | 85.7 | 3.8 |
| 3 | 93.4 | 26.3 |
| 4 | 66.2 | 1.7 |
| 5 | 83.6 | 2 |
| 6 | 94.9 | 25.1 |
| 7 | 96.5 | 37.1 |
| 8 | 96.3 | 38.9 |
| 9 | 98.6 | 33 |
| 10 | 97.8 | 32.1 |
| 11 | 97.3 | 32.8 |
| 12 | 98.4 | 21.8 |
| 13 | 92.4 | 29.9 |
| 14 | 92.9 | 85.1 |
| 15 | 98.1 | 97.1 |

EXAMPLE 6

Long-term Inhibition of Methane Production in Sheep

Materials & Methods: similar to Example 5 except that the dosages were administered in an intraruminal device at 700 mg of complex per 100 kg live weight. Specifically 16 g of formulation was delivered over a period of 43 days at an average delivery rate of 750 mg per 100 kg per day of formulation. The formulation comprised 89.5% of the complex made as in Example 1, 10% palmitic acid and 0.5% to 1.0% sodium dodecyl sulphate.

Results:

Table 3 shows that substantial methanogenic activity was provided for up to 43 days.

TABLE 3

Average methane production showing methane inhibition in sheep with formulation containing 0.5% SDS.

| Day | Ratio | % Hyd | % Meth |
|---|---|---|---|
| 0 | 0.00 | 0.31 | 99.69 |
| 1 | 217.28 | 99.54 | 0.46 |
| 3 | 110.05 | 98.87 | 1.13 |
| 10 | 292.77 | 99.58 | 0.42 |
| 15 | 258.91 | 99.61 | 0.39 |
| 18 | 414.81 | 99.76 | 0.24 |
| 22 | 391.53 | 99.74 | 0.26 |
| 25 | 6.33 | 85.21 | 14.79 |
| 29 | 282.89 | 99.65 | 0.35 |
| 32 | 402.82 | 99.75 | 0.25 |
| 36 | 328.75 | 99.70 | 0.30 |
| 39 | 402.12 | 99.75 | 0.25 |
| 43 | 42.33 | 97.12 | 2.88 |
| 46 | 0.19 | 15.39 | 84.61 |
| 50 | 0.14 | 11.88 | 88.12 |
| 53 | 0.12 | 11.04 | 88.96 |

EXAMPLE 7

Chances in Rumen Volatile Fatty Acid Composition

Changes in diet quality, and associated shifts in methane production, are normally accompanied by changes in the proportions of short chain volatile fatty acids in the rumen. Reduced acetate and increased propionate represents a shift from low to high molecular weight fatty acids and represents a more efficient use of nutrients in animals.

Materials & Methods: VFA were measured in accordance with standard gas liquid chromatography (GLC) analysis according to Supelco standard methods.

Cattle were fed two different diets; simulated pasture diet consisting of chaffed hay mixed with the antimethanogenic composition and a 70% concentrate diet. Animals on the 70% concentrate diet were given feed mixed with antimethanogenic composition alone (anti), Rumensin alone (Rum) and antimethanogenic composition and Rumensin (Anti and Rum) (see Tables 4 and 5). All treated animals were given a dose of 1.2 g complex/100 kg live weight per day. Control animals were given feed without any additives.

Results:

TABLE 4

Cattle weight gains on simulated pasture diet.

| Week | Treated | Control |
|---|---|---|
| (a) Cumulative Daily Liveweight Gains(Kgs) | | |
| 1 | 0.70 | 0.30 |
| 2 | 0.69 | 0.54 |
| 3 | 0.79 | 0.68 |
| 4 | 0.53 | 0.49 |
| 5 | 0.65 | 0.55 |
| 6 | 0.61 | 0.47 |
| 7 | 0.57 | 0.47 |
| 8 | 0.58 | 0.47 |
| 9 | 0.66 | 0.52 |
| 10 | 0.62 | 0.53 |
| 11 | 0.63 | 0.54 |
| 12 | 0.68 | 0.55 |
| (b) Feed Conversion Ratio | | |
| 1 | 9.68 | 22.60 |
| 2 | 10.11 | 12.94 |
| 3 | 9.05 | 10.41 |
| 4 | 13.15 | 14.12 |
| 5 | 10.81 | 12.67 |
| 6 | 11.42 | 14.62 |
| 7 | 12.14 | 14.55 |
| 8 | 11.87 | 14.45 |
| 9 | 10.44 | 13.13 |
| 10 | 11.18 | 12.83 |
| 11 | 11.05 | 12.67 |
| 12 | 10.25 | 12.44 |

TABLE 5

Cattle weight gains on concentrate diet.

| Week | Control | Anti | Rum | Anti+Rum |
|---|---|---|---|---|
| (a) Cumulative Daily Liveweight Gains (kgs) | | | | |
| 1 | 0.97 | −0.18 | 0.57 | −0.47 |
| 2 | 0.91 | 0.48 | 0.97 | 0.15 |
| 3 | 0.93 | 0.66 | 1.01 | 0.52 |
| 4 | 0.84 | 0.78 | 1.01 | 0.71 |
| 5 | 0.87 | 0.81 | 0.95 | 0.76 |
| 6 | 0.89 | 0.65 | 0.82 | 0.77 |
| 7 | 0.88 | 0.73 | 0.85 | 0.84 |
| 8 | 0.92 | 0.84 | 0.83 | 0.91 |
| 9 | 0.95 | 0.92 | 0.91 | 0.96 |
| 10 | 0.92 | 0.85 | 0.89 | 0.93 |
| 11 | 0.97 | 0.87 | 0.90 | 0.97 |
| 12 | 0.96 | 0.92 | 0.94 | 0.98 |
| (b) Feed Conversion Ratio | | | | |
| 1 | 11.96 | — | 16.54 | — |
| 2 | 12.65 | 15.1 | 9.79 | 38.62 |
| 3 | 12.46 | 11.96 | 9.33 | 12.25 |
| 4 | 13.82 | 10.64 | 10.21 | 9.80 |
| 5 | 13.39 | 10.46 | 11.14 | 9.95 |
| 6 | 13.05 | 12.77 | 12.81 | 10.09 |
| 7 | 13.09 | 11.37 | 12.43 | 9.69 |
| 8 | 12.51 | 9.98 | 12.49 | 9.17 |
| 9 | 12.03 | 9.27 | 11.46 | 8.82 |
| 10 | 12.37 | 10.25 | 11.66 | 9.24 |
| 11 | 11.73 | 10.07 | 11.55 | 8.95 |
| 12 | 11.75 | 9.65 | 11.14 | 9.01 |

Table 4 shows results obtained in the simulated pasture diet. Treated cattle consistently gained more weight and had better feed conversion ratios than untreated cattle.

Table 5 shows results obtained in the 70% concentrate trials. The results show that the combination of Rumensin and the antimethanogenic composition has an additive effect on weight gain in contrast to Rumensin alone or the antimethanogenic composition alone.

EXAMPLE 8

Effects in Sheep Wool

Weaner wethers (90), ranging between 25 and 35 kg in liveweight, were selected shortly after shearing in early October 1993. They were housed in individual pens for the following 154 days. The 154 days consisted of 5 periods of 21, 28, 42, 35 and 28 days respectively; these periods accorded to different dietary treatments and/or the times over which measurements of wool growth were carried out (see details below). Liveweights were recorded weekly and feed intakes daily during the time the sheep were held indoors The sheep were offered a medium-high quality, mixed roughage and concentrate diet ad libitum for 21 days (Period 1) while acclimatising to being held indoors. At the end of the period the ten animals with the lowest or most variable intakes were removed. For the following 28 days (Period 2) the remaining 80 sheep were fed 80% of the average of their ad libitum intake during the last 5 days of Period 1. During Period 2, and subsequent periods indoors, all sheep were also fed 125 g of a supplement, consisting of a mixture of lucerne chaff and hammer-milled lupins and oats. The supplement was always given and consumed prior to feeding the main ration.

At the end of period 2 the sheep were randomly allocated to one of 4 treatment groups (20 sheep/group), following stratification according to liveweight, liveweight gain and the rate of wool growth measured using mid-side patches during the latter half of the period (see Measurement of wool growth, etc for details). Sheep in 2 of the 4 groups were assigned to receive antimethanogen (AM) comprising the composition made in Example 1 in their daily supplement (+AM), with the other 2 groups remaining untreated (−AM). For the following 42 days (Period 3) sheep in one of the untreated groups were fed restricted amounts of a lower quality, roughage diet (Restricted; R), plus the supplement alone. Levels of intake were set, using the estimated metabolisable energy content of the diet and liveweight, so the sheep would lose approximately 50 g/d in liveweight. Sheep in one of the +AM groups were matched to those in the −AM group using liveweight and pair-fed the same diet plus the supplement; the supplement contained 340 mg of AM. This enabled a comparison of the effects of treatment on the efficiency of feed use and wool growth during liveweight loss, independent from possible effects on intake. All intakes were adjusted downward by 25 g/d on day 28 of the period to maintain liveweight losses. Sheep in the remaining A−AM and +AM groups were fed the same-diet ad libitum, plus their respective supplements (Unrestricted; U). Data from these 2 groups were used to assess the effects of AM on feed intake as well as production.

Period 4 was used to examine whether AM would affect the response in staple strength to acute changes in nutrition. For the first 18 days the feeding regimes were similar to those in Period 3, with a further reduction of 50 g/d in the roughage intakes of both the R groups from day 12 on. All sheep were then fed only their respective supplements for the following 3 day (days 19, 20 and 21). From day 22 onward, sheep in both the U and R groups were fed ad libitum on diet 1, plus their respective supplements. The level of AM in the supplement of the +AM sheep was increased to 370 mg/d to account for increases in liveweight of sheep in the U groups.

All sheep continued to be fed the same diet ad libitum plus supplements during the 28 days of period 5. This period was used to assess again the effects of the Am treatment on intake as well as production. Supplementation with the AM chemical ceased at the end of period 5 and the sheep were returned to the CSIRO farm. For the following 56 days, until shorn, they grazed dry, subterranean based, annual pasture and were supplemented 3 times a week with a mixture of oats and lupins. The supplementary feeding rate was equivalent to 250 g/head.day 1 with the ratio of oats to lupins being progressively altered from 1:2 to 2:1 over the first 4 weeks of supplementation.

Measurements

Rates of wool growth were assessed using both dyebands and by clipping approximately 100 $cm^2$ patches on the mid-side. Dyebands, which were applied to mid-side wool at the end of each Period, were removed 7 days prior to the sheep being shorn. Greasy wool weight (fleece+locks+belly) was recorded at shearing and a further sample of mid-side wool collected for determination of yield, clean wool weight and average fibre diameter by the Australian Wool Testing Authority. Wool growth rates in each period were then determined using greasy wool weight and the proportions of wool grown between dyebands in dyebanded staples. Rates of wool growth in Periods 2 to 6 were adjusted for yield.

Estimates of rates of wool growth using clipping were carried out more frequently than those using dyebands to try and minimise carry-over effects of dietary treatments. Mid-side areas were delineated at the end of Period 1 using a 10×10 cm square template. Wool was clipped from this area using Oster® clippers with a no. 44 blade and an accurate measurement made of the clipped area. Wool was reclipped from the same midside area on days 16 and 28 of Period 2 (Periods 2a and 2b), days 14 and 42 of Period 3 (Periods 3a and 3b), days 19 and 35 of Period 4 (Periods 4a and 4b) and day 28 of Period 5 (Period 5). Wool from the clipped patches was placed in a conditioning room for 24 hours before weighing. It was then washed twice with hot water containing detergent, rinsed thoroughly in clean water and dried in hot air before being placed in a desiccator for 24 hours. Samples were then reweighed and the clean weight calculated using an 18% regain. This weight and the area of the clipped patch were used to calculate rates of wool growth expressed as mg clean wool grown per day per $cm^2$.

Staple length and strength of wool from each sheep were determined using 5–8 dyebanded staples and Agritest (Sydney) length and strength testing instruments. The diameter of staples used for strength testing was restricted to between 0.8 and 1.1 mm. The position of break (POB), expressed as the percentage weight from tip, was measured by weighing the two halves of staples following staple strength determinations. Dyebands were also used to make visual observations on the period of growth in which the POB occurred. The time of the POB was calculated using the POB and rates of wool growth from dyeband measurements; linear rates of wool growth during each period were assumed.

The strength of the segments of staples grown during periods 2, 3, 4 and 5 were measured by clamping dyebanded staples at the edges of consecutive dyebands in the jaws of the Agritest staple strength tester. The tex measurements used for each segment (period) was the average of several measurements of staple diameter taken between the respective dyebands. Only 1–2 measurements were made for each staple segment because of the limited availability of dyebanded staples.

Subsamples of feed and the supplement, collected regularly during daily feeding, were oven dried at 90° C. for 24 h for determination of dry matter and dry matter intakes. Further samples of feed and feed ingredients were air dried and ground for determination of nitrogen and in vitro digestibility.

Wool-free liveweights were estimated using liveweight and measurements of rates of wool growth made using dyebands. These estimates were then used to calculate the daily rate of wool-free liveweight gain (positive or negative) for each week between liveweight measurements, for each of the intervals over which wool growth was measured using clipped patches, for each period and for the total time that sheep remained on the same dietary regime. The latter estimates were carried out using linear regression analysis with the weekly estimates of wool-free liveweight. These estimates excluded the first week's measurement after a change in diet or amount of feed offered so as to minimise changes in liveweight due to gut fill. Subsequently, the efficiency of feed use for liveweight gain during each of the various time intervals was calculated as wool free liveweight gain (+ or −) per day per g of dry matter intake.

Statistical analyses

All data, excluding dry matter intake, were analysed initially using simple analysis of variance with a 2 by 2 factorial design. Data from within each time interval where the feeding regimes were constant were also subjected to repeated measures analysis of variance, with and without covariates.

The relationship between the strength of the segment of staple in which the POB occurred and staple strength of the full staple was estimated for each treatment group using linear regression analysis. The relationships were then compared and, since they were found to be not significantly different, a common relationship was derived.

Results:

Liveweight, wool-free liveweight and wool-free liveweight change. Using WFLW2 as a covariate ($P<0.01$ to $0.001$) sheep in the U groups were significantly heavier ($P<0.001$) at all weighing times after the start of Period 3 (data not shown). These differences persisted after the sheep returned to the field. Small differences in liveweight which developed between the − and +AM groups during Periods 3 and 4a were not statistically significant. However, during the second half of period 4 (period 4b) and in period 5 +AM sheep were heavier ($P<0.05$) at 5 of the 7 weighings. This difference was still apparent at the last weighing in the field in May.

Identical results were obtained with wool-free liveweights although the effect of treatment with AM was reflected sooner in a higher wool-free liveweight gain (FIG. 2a) in the +AM sheep during Period 4a ($P<0.05;$). This was the result of a lower loss in liveweight in the R/+AM group and a higher liveweight gain in the U/+AM group. Similar effects were observed during Period 3 but the variability, both between weeks and between sheep within treatment groups, was high. Consequently, the difference of 7 g/d in wool-free liveweight gain between the R/+AM and R/−AM groups during the entire period of restricted intake, as calculated by linear regression, was not significant. Positive effects of the +AM treatment on wool-free liveweight gain were also observed at the ends of Periods 4 and 5 ($P<0.05$) and again in Period 6, after AM treatment had ceased. The higher, average daily gain by the +AM sheep of 6 g/d during Periods 4b and 5 was not significant.

Feed intake

Changes in the DMI are illustrated in FIG. 2b. This figure shows clearly that the difference in wool-free liveweight gain between the U/−AM and U/+AM groups in Period 4a was not due to a difference in DMI. The average DMI of these groups over Periods 3 and 4a were 932 and 916 g/d respectively. DMI of the +AM sheep was likewise marginally lower than that of the −AM sheep during Period 5 but the difference never approached significance.

Efficiency of feed use

The efficiency of feed use for wool-free liveweight gain, shown in FIG. 2c, tended to reflect changes in wool-free liveweight and wool-free liveweight gain. It was not influenced by any covariate measurements from Period 2. There were major effect of intake in Periods 3, 4 and 5 ($P<0.01$ to $P<0.001$). R groups tended to have the higher efficiency during Period 4b and in the first 3 weeks of period 5. However, by week 4 of Period 5 Intake had no effect. AM treatment lead to a small but significantly higher efficiency in the R group at the end of Period 3 and again in Period 4a ($P<0.05$). Over the time that all sheep were fed the higher quality diet ad libitum during Periods 4b and 5, efficiency was marginally higher again in the R/+AM group ($P=0.07$).

Wool growth and quality

Rate of wool growth in Period 2 was significant when used as a covariate in analyses of rates of wool growth but had no effect with measurements involving the whole fleece. On the other hand WFLW2 was significant to varying degrees when used as a covariate in both sets of analyses. Neither greasy nor clean wool production were affected by AM treatment although both were higher in the U groups ($P<0.0.01$) (data not shown). In contrast, Intake had no significant effect on fibre diameter but there was significantly reduced by the AM treatment ($P<0.05$). The average fibre diameter of +AM groups was approximately 0.7 mm lower than that of the −AM groups. Neither intake nor AM treatments had any effect on staple length but the staple strength of the R groups was some 12 N/ktex lower than that of the U groups ($P<0.001$). POB in the R groups was also some 4.6% higher ($P<0.001$) This difference translated into a 10 day difference in the mean time of the POB ($P<0.001$). The average times of the POB in the U and R groups were day 1 and day 11 of Period 4 respectively. Both these times were before the sudden changes in nutrition. There was no effect of the AM treatment on staple strength, POB or time of POB.

Analysis of the rates of wool growth measured using dyebands (FIG. 3), using the rate of wool growth in period 2 as a covariate, showed significant effects of Intake in Periods 3 ($P<0.01$), 4 ($P<0.001$) and 5 ($P<0.05$). Rates of wool growth were higher in the U groups of sheep from period 3 onward. AM treatment was without effect. When data from all periods from period 2 onward were analysed using repeated measures analysis of variance, Intake and Period of growth were significant ($P<0.001$), with a significant. Period of growth×Intake interaction ($P<0.001$).

Comparing rates of wool growth using clipped patches (FIG. 4), with the rate of growth in period 2b as a covariate, also showed that the U groups had higher rates of wool growth in all periods after Period 3a. ($P<0.001$). Differences between the U and R groups in Period 5 were more pronounced than seen using dyeband measurements. The rate of wool growth was also marginally lower in the +AM groups in several periods but this difference was significant only in Period 3b ($P<0.05$). Repeated measures analysis of variance again showed a significant effect of Intake ($P<0.001$) and different changes in rate of growth of the U and R groups over time ($P<0.001$). A possible Period of growth×AM interaction was also indicated ($P=0.07$). This appeared to arise from a relatively sharper decline in rate of growth in Period 3a and smaller increase in Period 5 in the +AM group compared with the −AM.

Changes in staple strength were observed. Segment strength was consistently lower for the R groups in Periods 3 ($P<0.01$), 4 ($P<0.001$) and 5 ($P<0.05$). AM treatment had no effect. Likewise, there were no apparent effects of the changes in nutrition in Period 4. The segments of the staple with the lowest strength were all grown in period 5; this contrasted with the times of the POB. A highly significant linear relationship was found between the strength of the full staple and the strength of the segment in which the POB occurred ($P<0.001$).

The absence of any significant effect on the +AM treatment on rates of wool growth was unexpected. The reduced fibre diameter was extremely surprising given the absence of increased wool growth rates and the fact that there were no alterations in staple length. It was also surprising that sound wool was produced in the R groups despite a 7 to 8% weight loss.

EXAMPLE 9

Heliotrope Detoxification

The inhibition of methane within the rumen of sheep and cattle increases the availability of hydrogen to hydrogen utilising bacteria such as *Peptostreptococcus heliotrinereducans*, a microbe which leads to the reductive breakdown of pyrrolizidine alkaloids.

Materials & Methods:

The concentrations of heliotrine and other major pyrrolizidine alkaloid in heliotrope in the rumen of sheep were measured. The sheep were fed a diet comprising 50% heliotrope and 50% oaten-lucerne chaff given once per day. Treated sheep were administered with a sheep capsule carrying the previously described formulation delivering an average of 330 mg of complex per sheep per day. Samples of the rumen contents were taken 24 hours after feeding, frozen and then analysed for heliotrine.

Results:

A significant reduction was observed over the first 40 days in rumen pyrrolizidine alkaloid concentrations of sheep treated with the antimethanogen formulation. This is a significant effect. During this initial 40 day period normal untreated sheep are at their most inefficient in terms of their ability to degrade pyrrolizidine alkaloids. In the treated sheep the antimethanogen augments the detoxification action of *P. heliotrinreducans*, as described by Lanigan (1971, 1972), by making hydrogen, an apparently essential substrate in the detoxification reaction, more available in the rumen. Compared to controls, treated sheep more efficiently break down the pyrrolizidine alkaloids during the critical period when animals are first exposed to the toxins in their diet. After a 40 day induction period, in which the detoxification activity of *P. heliotrinreducans* increases, the untreated control sheep become as efficient as the treated sheep in breaking down pyrrolizidine alkialoids in their rumen.

EXAMPLE 10

Trials with Antimethanogen and a Hormone

Materials & Methods

The composition described in Example 1 was used as a feed additive in a cattle productivity trial feeding a baled pasture diet formulated to simulate a typical tropical wet season diet. The trial consisted of four groups of cattle two receiving the antimethanogenic additive and two being implanted with a hormone growth promotant, (Compudose 100), in a typical 2×2 trial design.

Weekly liveweight changes and daily feed intake were measured and overall feed conversion efficiency for the treatment period was calculated.

Results:

| Live weight gains | |
|---|---|
| Control animals | 0.585 Kg/Day |
| Antimethanogen | 0.617 |
| Compudose 100 | 0.714 |
| Compudose + antimethanogen | 0.798 |

| -continued | |
|---|---|
| Dry Matter intake | |
| Control animals | 18.71 g/KgLW/Day |
| Antimethanogen | 16.87 |
| Compudose 100 | 19.07 |
| Compudose + antimethanogen | 18.17 |
| Feed Conversion efficiency | |
| Control animals | 8.0 kgDM/kg liveweight |
| Antimethanogen | 7.1 |
| Compudose 100 | 6.78 |
| Compudose + antimethanogen | 6.0 |

Thus the animals fed the antimethanogen compudose had better live weight gains and feed conversion efficiencies than the animals fed antimethanogen alone and the control animals.

This demonstrates that the composition of the present invention may be used in conjunction with commercially available products and still produce the desired effects.

References

Budai Z. S. & Szejtli J. "Recovery of solvent vapours from gaseous phase by solvent solutions" I. Int. Symp. on Cyclodextrins, Budapest, 1981.
Lanigan, G. W. (1971) Aust. J. Agric. Res 22:123–130.
Lanigan, G. W. (1972) Aust. J. Agric. Res 23:1085–1091
Trei, J. E. & Olson, W. A. (1969) J. Anim. Sci 29:173
Johnson, E. D. et al (1972) Con. J. Anim. Sci. 52:703–712

We claim:

1. A composition for use in animals comprising a volatile and/or water soluble antimethanogenic agent together with cyclodextrin or a cyclodextrin-like compound such that sustained release of said agent is provided, wherein said antimethanogenic agent is at least partly enclosed in, confined by, or encapsulated by said cyclodextrin or cyclodextrin-like compound.

2. The composition of claim 1 wherein said composition comprises a delivery system for delivering said volatile and/or water soluble antimethanogenic agent to an animal.

3. An animal feed comprising an antimethanogenic composition, said antimethanogenic composition comprising a volatile and/or water soluble antimethanogenic agent together with a cyclodextrin or a cyclodextrin-like compound such that sustained release of said agent is provided, wherein said antimethanogenic agent is at least partly enclosed in, confined by, or encapsulated by said cyclodextrin or cyclodextrin-like compound.

4. The composition of claim 1 or the animal feed of claim 3 wherein said antimethanogenic agent is selected from the group consisting of bromochloromethane, analogues of bromochloromethane, halothane and 2-bromoethane sulphonate.

5. A method of improving weight gain in a ruminant comprising administering to said ruminant an effective amount of the composition of claim 1 for a time and under conditions sufficient to allow weight gain to occur.

* * * * *